(12) United States Patent
Lee et al.

(10) Patent No.: US 10,272,272 B2
(45) Date of Patent: Apr. 30, 2019

(54) HIGH-INTENSITY FOCUSED ULTRASOUND OPERATION DEVICE AND OPERATION METHOD THEREOF

(71) Applicant: HIRONIC CO., LTD., Seongnam-si, Gyeonggi-do (KR)

(72) Inventors: Jin U Lee, Seongnam-si (KR); Sung Won Lee, Yongin-si (KR)

(73) Assignee: Hironic Co., Ltd. (KR)

( * ) Notice: Subject to any disclaimer, the term of this patent is extended or adjusted under 35 U.S.C. 154(b) by 149 days.

(21) Appl. No.: 14/906,498

(22) PCT Filed: Nov. 11, 2014

(86) PCT No.: PCT/KR2014/010819
§ 371 (c)(1),
(2) Date: Jan. 20, 2016

(87) PCT Pub. No.: WO2015/141921
PCT Pub. Date: Sep. 24, 2015

(65) Prior Publication Data
US 2016/0175619 A1    Jun. 23, 2016

(30) Foreign Application Priority Data

Mar. 18, 2014  (KR) .................. 10-2014-0031722
Mar. 26, 2014  (KR) .................. 10-2014-0035541
Jul. 26, 2014   (KR) .................. 10-2014-0095158

(51) Int. Cl.
*A61N 7/00*     (2006.01)
*A61N 7/02*     (2006.01)
*A61B 18/00*    (2006.01)

(52) U.S. Cl.
CPC .............. *A61N 7/02* (2013.01); *A61N 7/022* (2013.01); *A61B 2018/00452* (2013.01);
(Continued)

(58) Field of Classification Search
CPC ............ A61N 7/00; A61N 7/02; A61N 7/022
(Continued)

(56) References Cited

U.S. PATENT DOCUMENTS 5,527,331 A     6/1996 Kresch et al.
2007/0232913 A1  10/2007 Lau et al.
(Continued)

FOREIGN PATENT DOCUMENTS

EP     0 659 387 A2    6/1995
JP     H02-239856 A    9/1990
(Continued)

OTHER PUBLICATIONS

Japanese Office Action dated Feb. 7, 2017 from Japanese Application No. 2016-531563, 4 pp.
(Continued)

*Primary Examiner* — Carolyn A Pehlke
(74) *Attorney, Agent, or Firm* — Brinks Gilson & Lione

(57) ABSTRACT

Disclosed herein is a high-intensity focused ultrasound operation device including a handle part for manipulation by an operator, an insertion part provided at the front end of the handle part and inserted into a vagina during operation, an ultrasound treatment transducer provided to the insertion part to generate high-intensity focused ultrasound, a driver for driving the ultrasound treatment transducer, and a controller for controlling the driver. The high-intensity focused ultrasound operation device may be utilized for a variety of operations such as beauty treatment, adipolysis, gynecological disease treatment, etc.

16 Claims, 11 Drawing Sheets

(52) U.S. Cl.
CPC ............... *A61B 2018/00559* (2013.01); *A61N 2007/0008* (2013.01); *A61N 2007/0034* (2013.01); *A61N 2007/0043* (2013.01); *A61N 2007/0065* (2013.01); *A61N 2007/0091* (2013.01); *A61N 2007/0095* (2013.01)

(58) Field of Classification Search
USPC .............................................. 601/2; 600/437
See application file for complete search history.

(56) References Cited

U.S. PATENT DOCUMENTS

2012/0016239 A1\* 1/2012 Barthe ................. A61B 8/0858
                                                      600/439
2012/0035473 A1     2/2012 Sanghvi et al.

FOREIGN PATENT DOCUMENTS

| JP | H07-227394 A | 8/1995 |
|---|---|---|
| JP | 2001-514921 | 9/2001 |
| JP | 2004-154256 A | 6/2004 |
| JP | 2005-124920 | 5/2005 |
| JP | 2005-516663 | 6/2005 |
| JP | 2008-515559 A | 5/2008 |
| JP | 2008-535568 | 9/2008 |
| JP | 2010-515558 | 5/2010 |
| JP | 2011-522625 A | 8/2011 |
| KR | 10-2007-0065332 | 6/2007 |
| KR | 10-2011-0020293 | 3/2011 |
| KR | 10-2011-0091831 | 8/2011 |
| KR | 10-2011-0091832 | 8/2011 |
| KR | 10-2011-0121701 | 11/2011 |
| KR | 2012-80948 A | 4/2012 |
| KR | 10-2012-0100049 | 9/2012 |
| KR | 10-2012-0116908 | 10/2012 |
| KR | 10-1191347 | 10/2012 |
| KR | 10-1307551 | 9/2013 |
| WO | 2006/104568 A1 | 10/2006 |

OTHER PUBLICATIONS

International Search Report dated Feb. 4, 2015 in International Application No. PCT/KR2014/010819.
Extended European Search Report dated Sep. 28, 2016 in EP 14885955, published as EP3017845 on May 11, 2016, 7pp.
Japanese Office Action dated Jul. 11, 2017 issued from corresponding Japanese Patent Application 2016-531563, 2pp.
Japanese Notice of Completion of Pre-appeal Reconsideration dated Dec. 7, 2017 in connection with the counterpart Japanese Patent Application No. 2016-531563, 2p.

\* cited by examiner (a)

(b)

(a)　　　　　　　　(b)

HIGH-INTENSITY FOCUSED ULTRASOUND OPERATION DEVICE AND OPERATION METHOD THEREOF

This application is the U.S. National Stage under 35 U.S.C. § 371 of International Patent Application PCT/KR2014/010819, filed Nov. 11, 2014, which claims the benefit of Korean Patent Application 10-2014-0031722 filed on Mar. 18, 2014, Korean Patent Application No. 10-2014-0035541 filed on Mar. 26, 2014 and Korean Patent Application No. 10-2014-0095158 filed on Jul. 26, 2014. These applications are incorporated by reference herein in their entirety.

TECHNICAL FIELD

The present invention relates a high-intensity focused ultrasound operation device and an operation method thereof.

BACKGROUND ART

Recently, interest in skin care and obesity treatment is increasing day by day. Accordingly, various medical devices for skin care and obesity treatment are being developed. For example, various skin care medical products for patients who want face lifting or skin tightening operations are being developed. Medical devices for obesity treatment are also being developed.

Examples of medical devices for skin care include medical devices to incise skin tissue in an invasive manner. However, such a manner has safety issues of operation and is not preferred by patients. Accordingly, non-invasive medical devices that do not require incision of skin tissue are increasingly attracting attention. Such a trend becomes dominant in skin care and obesity treatment, and is expected to prevail in other medical fields as well.

To meet such a trend, ultrasound medical devices using high-intensity focused ultrasound (HIFU) are coming into the spotlight as non-invasive medical devices. For example, there are ultrasound medical devices for non-invasively performing skin lifting or skin tightening operations by irradiating high-intensity focused ultrasound onto the interior of skin tissue for skin care operation, and an ultrasound medical device for non-invasively burning or dissolving fat tissue by irradiating high-intensity focused ultrasound (HIFU) onto a subcutaneous fat layer for obesity treatment.

Incidentally, gynecological disease patients are ever increasing. In general, gynecological diseases can be roughly classified into neoplastic disease, inflammatory diseases, menstrual disorders, venereal diseases, sexual dysfunction, etc. More particularly, there are cervical cancer, ovarian cancer, etc., as examples of representative cancers and there is hysteromyoma as an example of neoplastic disease. There is leucorrhea as an example of inflammatory disease and amenorrhea, menstrual pain, menstrual cycle disorder, etc., as examples of menstrual disorders. In addition, there are sexual desire disorder, sexual arousal disorder, orgasmic disorder, dyspragia, vaginal contraction disorder, etc., as examples of sexual dysfunction. Among these, sexual dysfunction refers to inability to achieve orgasm or other sex-related difficulties. Traditionally, sexual dysfunction in women naturally occurs due to childbirth or aging in many cases. However, recently, sexual dysfunction patients are ever increasing even among young women in their 20s to 30s. In regard to such phenomenon, there are various causes, but immoderate smoking and drinking, drug abuse, stress, etc., are known as major causes of increase in sexual dysfunction among young people.

Treatment methods of such gynecological diseases can be roughly classified into treatment methods using drugs and treatment methods using medical devices. Among these, treatment methods using medical devices for gynecological disease treatment include using thermal medical devices, moxa-cauterizers, sitz bath devices, laser therapy devices, etc. However, treatment methods using thermal medical devices, moxa-cauterizers, sitz bath devices, etc., are not direct treatment methods and it is known that effects thereof are also very trivial. In addition, for a treatment method using laser therapy devices, bleeding comes along with intense pain during operation, and pain persists even after operation and side effects occur. Accordingly, daily life becomes very uncomfortable.

RELATED ART DOCUMENT

US Patent Application Publication No. 2007-0232913

DISCLOSURE

Technical Problem

It is an object of the present invention to provide non-invasive gynecological disease treatment and vaginal contraction operations. It is another object of the present invention to provide increase safety and efficiency of the operations for gynecological disease treatment and vaginal contraction. It is another object of the present invention to provide different types of operations by means of a single device. It is yet another object of the present invention to increase operation efficiency by shortening operation time.

Technical Solution

In accordance with one aspect of the present invention, provided is a high-intensity focused ultrasound operation device, including: a handle part for manipulation by an operator; a cartridge provided at a front end of the handle part and inserted into a vagina during operation; an ultrasound treatment transducer provided at the cartridge and generating high-intensity focused ultrasound (HIFU); a driver for driving the ultrasound treatment transducer; and a controller for controlling the driver.

In this case, the ultrasound treatment transducer may include at least one independent transducer that forms a single thermal lesion with the high-intensity focused ultrasound at a location spaced apart from a vaginal inner-wall surface by a predetermined distance or at least one transducer array that forms multiple thermal lesions with the high-intensity focused ultrasound.

In addition, the cartridge may have a cylinder or bar shape and include a window which is formed in a longitudinal direction of the cartridge at a circumference of the cartridge and through which high-intensity focused ultrasound generated from the ultrasound treatment transducer is transmitted.

In addition, the ultrasound treatment transducer may irradiate high-intensity focused ultrasound toward endopelvic fascia (EPF).

In addition, the ultrasound treatment transducer may irradiate the high-intensity focused ultrasound to a depth of 1.0 to 30.0 mm from a vagina surface.

In addition, the driver may include a stepper motor enabling the ultrasound treatment transducer to perform straight-line back-and-forth motion within a range of 10.0 mm to 120.0 mm.

In addition, the cartridge may have a cylinder or bar shape and the driver may include a rotation motor for rotating the cartridge within a range of 30 to 360 degrees.

In addition, the controller may control the driver such that thermal lesions caused by high-intensity focused ultrasound of the ultrasound treatment transducer form a straight line or a plurality dots of arranged on a string line during operation.

In addition, an image probe provided at the cartridge and imaging an area irradiated with high-intensity focused ultrasound of the ultrasound treatment transducer may be further included.

In this case, the image probe may be coupled with the ultrasound treatment transducer.

In addition, in an embodiment, a cooling fluid provided in the cartridge; and a cooling fluid circulation line for supplying the cooling fluid to the cartridge and retrieving the supplied cooling fluid may be further included.

In accordance with another aspect of the present invention, provided is a high-intensity focused ultrasound operation device for use in operations for gynecological disease treatment or a vaginal contraction, the high-intensity focused ultrasound operation device including: a first cartridge forming a thermal lesion through high-intensity focused ultrasound; a second cartridge forming a smaller high-intensity focused ultrasound thermal lesion than the first cartridge; an operation handpiece designed compatibly with the first and second cartridges; and a driver provided at the operation handpiece and used compatibly with the first and second cartridges to drive the first and second cartridges.

In an embodiment, an image probe provided at the operation handpiece and used compatibly with first and second cartridges to image a high-intensity focused ultrasound irradiation area irradiated by each of the first and second cartridges may be further included.

In addition, the image probe is provided at each of first and second cartridges, and the image probe is coupled with the ultrasound treatment transducer to be integrally provided with the ultrasound treatment transducer.

In accordance with another aspect of the present invention, provided is a high-intensity focused ultrasound operation device, including: an operation handpiece used as a handle of an operator; a cartridge having a bar shape in order to be inserted into a vagina of a operation subject, detachably provided to the operation handpiece, and including an ultrasound treatment transducer generating high-intensity focused ultrasound in an interior of the cartridge; and a driver for driving the ultrasound treatment transducer such that the ultrasound treatment transducer moves from front to back in a longitudinal direction of the cartridge, wherein the operation handpiece includes a cartridge-rotating part for rotating the cartridge with respect to a rivet of the cartridge.

In addition, a guider for fastening with the cartridge may be provided at the operation handpiece, and a fastener may be provided, in a shape corresponding with the guider, at the cartridge to be fastened with the guider.

In addition, the cartridge may be set such that the high-intensity focused ultrasound is irradiated to a depth of 1.0 to 30.0 mm from a vagina inner-wall surface.

In accordance with another aspect of the present invention, provided is a high-intensity focused ultrasound operation method, the method including: preparing a cartridge having an ultrasound treatment transducer generating high-intensity focused ultrasound; inserting the cartridge into a vagina of a subject; and controlling the ultrasound treatment transducer such that a thermal lesion caused by the high-intensity focused ultrasound of the ultrasound treatment transducer is formed at a location spaced apart from a vaginal inner wall by a predetermined distance.

In accordance with yet another aspect of the present invention, provided is a method of operating high-intensity focused ultrasound, the method including: preparing a first handpiece assembly for skin care treatment; preparing a second handpiece assembly for gynecological disease treatment and vaginal contraction operations; and selecting an operation type for a subject to be operated; and operating the high-intensity focused ultrasound using any one of the first and second handpiece assemblies that is suitable for the selected operation type.

Advantageous Effects

A high-intensity focused ultrasound operation device according to an embodiment of the present invention may include cartridges, compatible with the operation handpiece, having operation conditions suitable for subjects to be operated, and a cartridge selected therefrom is mounted to the operation handpiece and used for an operation. Accordingly, patient-specific operations may be conducted by means of only one device through cartridge changing. In addition, since the high-intensity focused ultrasound may non-invasively regenerate or recover endopelvic fascia controlling vaginal contraction using high-intensity focused ultrasound, pain is minimal and bleeding hardly occurs, compared to laser devices that directly burn a vaginal inner wall. Therefore, the patient can live an ordinary life after operation.

According to an embodiment of the present invention, an operator may form thermal lesions over an entire vaginal inner wall while combining front-to-back movement and rotation of the ultrasound treatment transducer, by simply manipulating the operation handpiece, thereby shortening time taken for gynecological disease treatment and/or vaginal contraction operations and enhancing operation efficiency.

According to an embodiment of the present invention, two or more high-intensity focused ultrasound operations may be conducted using a single device by mounting a cartridge, to an operation handpiece, suitable for a desired operation among a face lifting or skin tightening operation, a subcutaneous fat layer reduction or removal operation, and operations for gynecological disease treatment and vaginal contraction to an operation handpiece and conducting the operation after preparing cartridges having various operation purposes compatibly with the operation handpiece.

A high-intensity focused ultrasound operation method according to an embodiment of the present invention may perform an operation customized for each patient by means of a single device by changing a cartridge since the operation may be conducted by, after preparing cartridges having an operation condition suitable for a state of a subject to be operated compatibly with an operation handpiece, mounting a selected cartridge on the operation handpiece.

MODE FOR INVENTION

Figure 1:
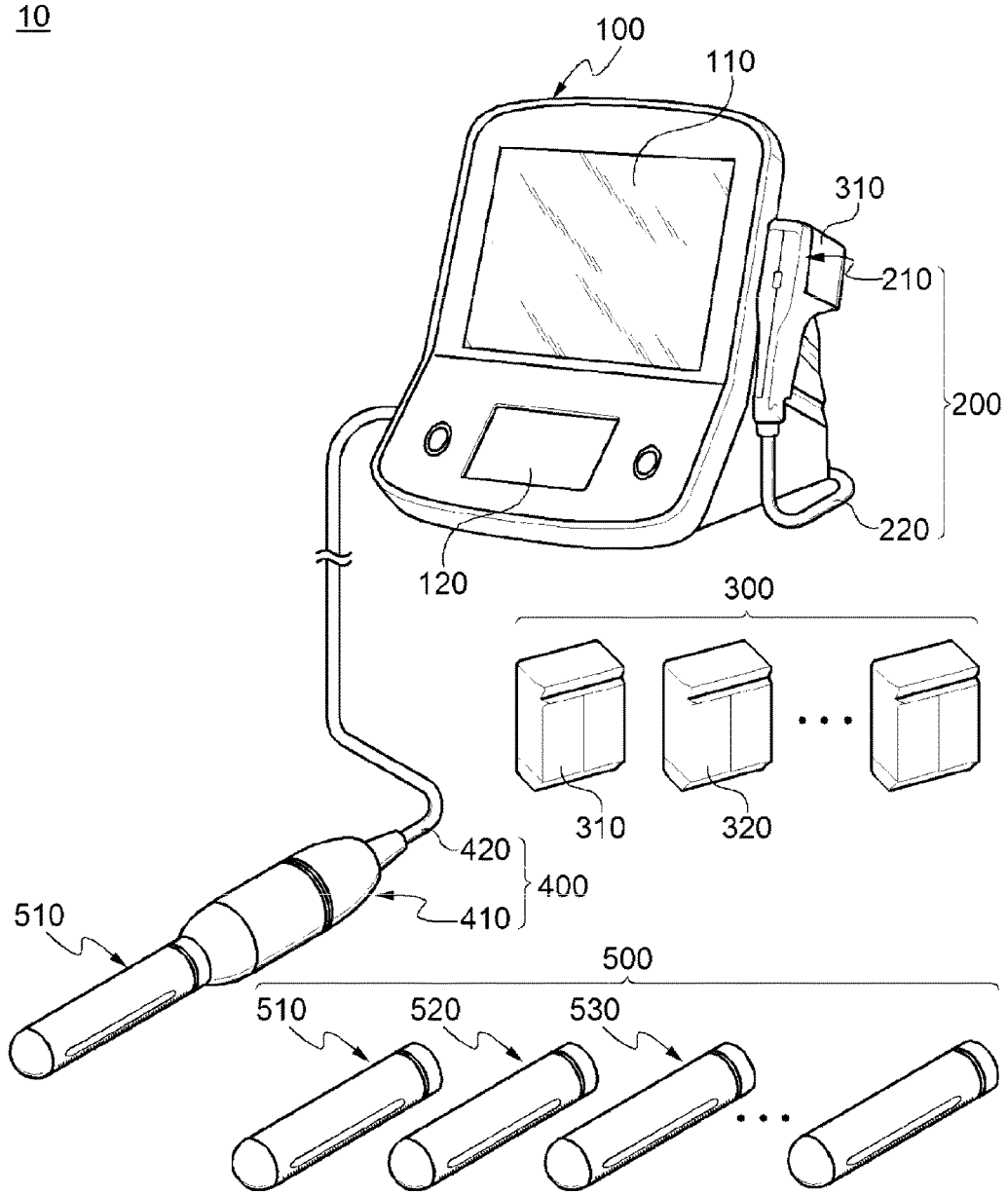
FIG. 1 is a perspective view schematically illustrating a high-intensity focused ultrasound operation device according to an embodiment of the present invention.
Figure 2:
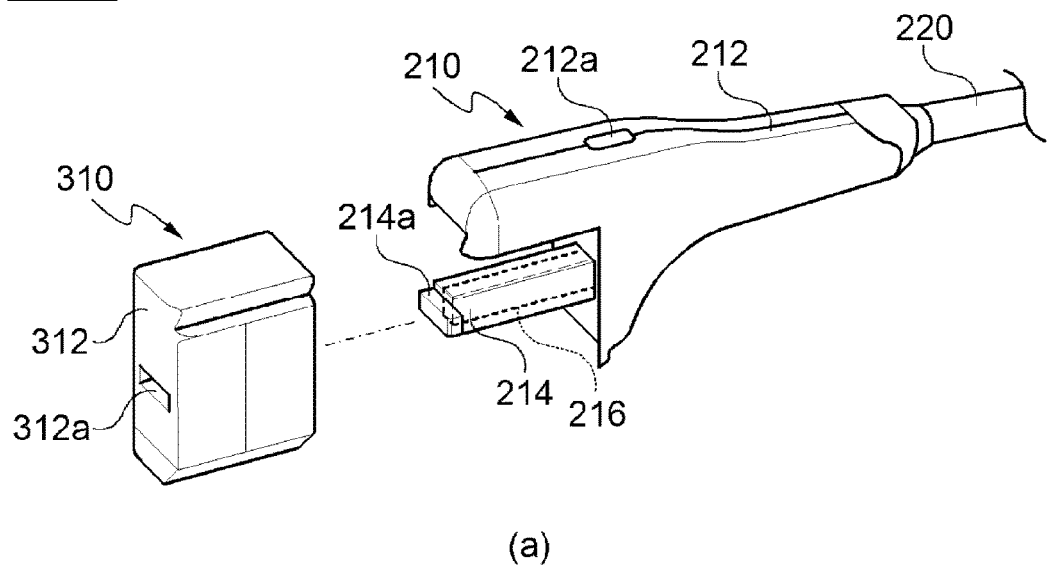
FIG. 2 is a view illustrating a coupling process of a first operation handpiece and a first cartridge illustrated in FIG. 1.
Figure 2:
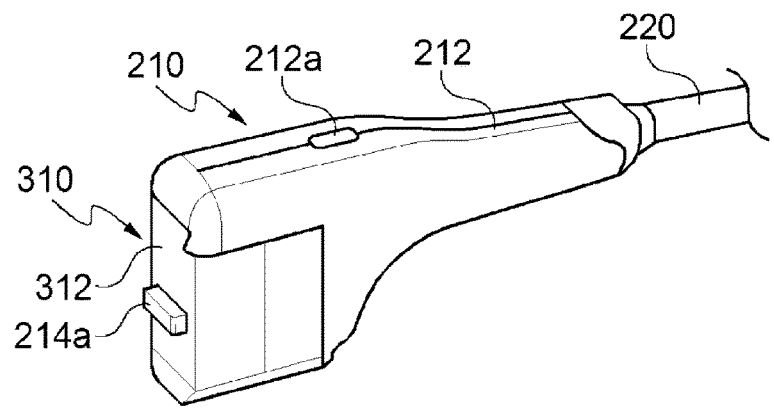
Figure 3:
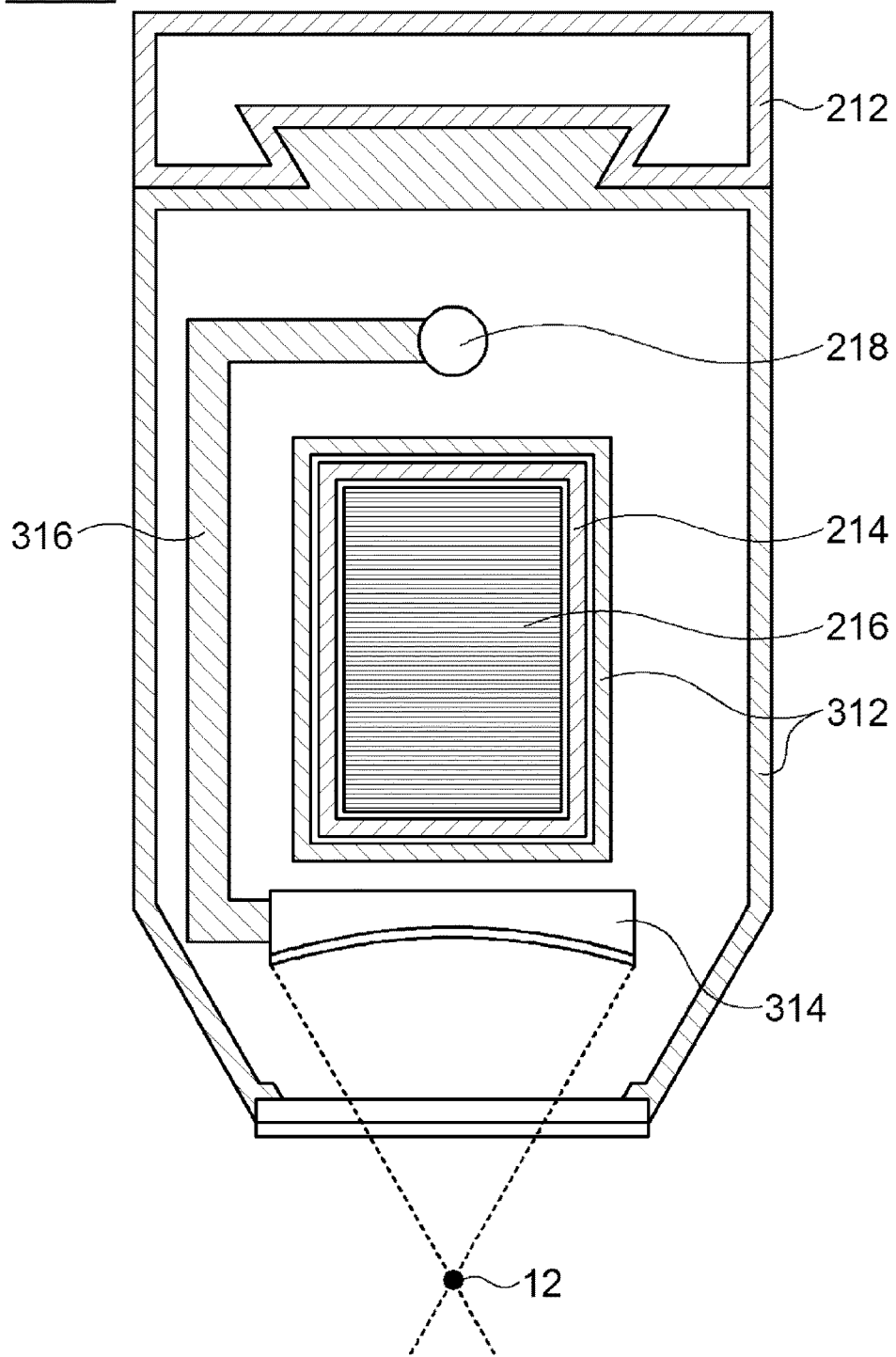
FIG. 3 is a sectional view schematically illustrating a first operation handpiece and a first cartridge illustrated in FIG. 1.

Referring to FIGS. 1 to 3, a high-intensity focused ultrasound operation device 10 according to an embodiment of the present invention may be an ultrasound medical device for conducting operations for gynecological disease treatment and/or vaginal contraction using high-intensity focused ultrasound (hereinafter referred to as "HIFU"). In addition, the high-intensity focused ultrasound operation device 10 may be a medical device that may conduct two or more different operations using high-intensity focused ultrasound (HIFU). In this case, the two or more operations basically are operations for gynecological disease treatment and/or vaginal contraction and may additionally include at least one of a non-invasive face lifting operation or a skin tightening operation, and operations to reduce or remove non-invasive subcutaneous fat layers.

The high-intensity focused ultrasound (hereinafter referred to as "HIFU") may form a thermal lesion 12 by focusing such that ultrasound is concentrated on one focal point. The thermal lesion 12 may be a thermal focus having a high temperature of about 60° C. or more. Accordingly, the high-intensity focused ultrasound operation device 10 conducts a face lifting operation or a skin tightening operation by forming the thermal lesion 12 on dermis, fascial layers, or SMAS layers at a location about 1.5 mm to 4.5 mm from a skin surface, or an operation to reduce or remove fat by forming the thermal lesion 12 on subcutaneous fat layers at a location about 6.0 mm to 15.0 mm from a skin surface. Alternatively, operation of regenerating or recovering endopelvic fascia (EPF, see 70 in FIG. 11) may be conducted through formation of thermal lesions (22 in FIG. 11) on the endopelvic fascia as muscle controlling vaginal contraction in women.

The high-intensity focused ultrasound operation device (hereinafter referred to as "HIFU operation device 10") may include a device body 100, a first handpiece assembly 200, a first cartridge set 300, a second handpiece assembly 400, a second cartridge set 500, etc.

The device body 100 may provide operation-related information to an operator (not shown) and enable the operator to operate or manipulate the HIFU operation device 10. For example, the device body 100 may include a display 110 for displaying operation-related information to an operator, a controller 120 enabling the operator to operate or control the HIFU operation device 10, etc. As the controller 120, a touch screen, etc. may be used.

The first handpiece assembly 200 may include a first operation handpiece 210 and a first connection cable 220. The first operation handpiece 210 provided to irradiate HIFU to an operation subject may be provided in a hand-held form in order to provide more convenient manipulation to a user. For example, the first operation handpiece 210 may include a first handle part 212 such that an operator conveniently holds the first operation handpiece 210. A first operation switch 212a enabling an operator to control ultrasound irradiation operation may be provided to an upper portion of the first handle part 212. The first connection cable 220 may electrically and physically connect the first operation handpiece 210 and the device body 100. One end of the first connection cable 220 is connected with the first operation handpiece 210 and another end of the first connection cable 220 may be detachably connected to the device body 100.

The first cartridge set 300 may be composed of a plurality of cartridges. For example, the first cartridge set 300 may include a first cartridge 310 and a second cartridge 320, operation conditions of which are different. Operation purposes of the first cartridge 310 and the second cartridge 320 are different. Particularly, the first cartridge 310 may serve to reduce or remove a non-invasive subcutaneous fat layer and the second cartridge 320 may be used for a non-invasive face lifting operation or a skin tightening operation. Detailed descriptions such as an operation process and an operation condition for each of the first and second cartridges 310 and 320 are described below.

Each of the first and second cartridges 310 and 320 may be detachable from the first operation handpiece 210. For example, a first guider 214 for coupling with a cartridge (310 in FIG. 2, etc.) of the first cartridge set 300 may be provided at a front end of the first handle part 212. In an embodiment, the first guider 214 may be provided in a bar shape protruded in a front end direction of the first handle part 212. In addition, a penetrated hole 312a having a shape corresponding to a cross-section of the first guider 214 is provided at the center of a first cartridge body 312. Accordingly, as illustrated in FIG. 2(a), the first cartridge 310 may be coupled to the first operation handpiece 210 by inserting the first guider 214 into the penetrated hole 312a. In this case, in order to prevent a coupled state of the first cartridge 310 from being released, a locking device 214a may be provided at a front end of the first guider 214. An operator may lock the first cartridge 310 by rotating the locking device 214a or release a locked state thereof.

To the interior of the first guider 214, a first image probe 216 for imaging tissue to be operated upon may be provided. Mostly, the first image probe 216 may be provided in a bar type according to the first guider 214. The first image probe 216 may generate image ultrasound in order to image skin tissue to be operated upon, i.e., a subcutaneous fat layer. The first guider 214 may be located at an upper portion of the therapeutic transducer 314 provided to each of the first and second cartridges 310 and 320 when the first and second cartridges 310 and 320 are fastened with the first operation handpiece 210. Accordingly, the therapeutic transducer 314 irradiates HIFU while moving from front to back at an under portion of the first guider 214, and thus, the therapeutic transducer 314 may be called an ultrasound treatment transducer. In addition, the first image probe 216 may generate separate image ultrasound to image a subcutaneous fat layer, and display the image through the display 110.

Here, the first operation handpiece 210 may include a first driver 218 in order to move the therapeutic transducer 314 from front to back. In an embodiment, as the first driver 218, a stepper motor, etc. may be used. The first driver 218 and the therapeutic transducer 314 may be connected by a supporter 316. Accordingly, the first driver 218 causes the supporter 316 to move from front to back and thus the therapeutic transducer 314 may move from front to back.

The first driver 218 may enable the therapeutic transducer 314 to move from front to back such that the therapeutic transducer 314 has an operation range of about 40.0 mm to 100.0 mm. More particularly, the first driver 218 may be a stepper motor and enable the therapeutic transducer 314 to move from front to back by a predetermined length within a range of about 40.0 mm to 100.0 mm. In this case, the therapeutic transducer 314 may irradiate HIFU during moving within this range. The therapeutic transducer 314 may be set in such a way that HIFU is irradiated at a regular interval such that the thermal lesion 12 forms a plurality of dots along the same line, or in such a way that HIFU is irradiated such that the thermal lesion 12 forms a straight line without an interval.

Meanwhile, when a moving length from front to back of the therapeutic transducer 314 is less than 40.0 mm, an operation area that is subject to skin lifting, skin tightening or a subcutaneous fat layer operation is small, whereby operation time may be greatly prolonged. The subcutaneous fat layer curvedly spreads in both directions with respect to the navel of the human. Accordingly, when the moving range from front to back of the therapeutic transducer 314 is greater than 100.0 mm, initial and final HIFU irradiation depths for the subcutaneous fat layer become different because the therapeutic transducer 314 is set in such a way that HIFU is irradiated to a regular depth, whereby the risk that HIFU is irradiated to an area outside a subcutaneous fat layer may increase. Such a risk may similarly occur also in the case of skin lifting or skin tightening. Accordingly, the first driver 218 may be set such that the therapeutic transducer 314 moves from front to back within a range of about 40.0 mm to 100.0 mm, more preferably 60.0 mm to 80.0 mm, in order to reduce operation time while securing operation safety.

Meanwhile, each of the first and second cartridges 310 and 320 may include a cooling fluid for cooling heating generated due to operation of the therapeutic transducer 314. In an embodiment, each of the first and second cartridges 310 and 320 is provided such that the interior thereof may be filled with cooling water, and the cooling water is set to be circulated via a separate cooling water circulation line (not shown), thereby preventing overheating of the therapeutic transducer 314. In order to realize this, when the first and second cartridges 310 and 320 are mounted to the first operation handpiece 210, the cooling water in the first and second cartridges 310 and 320 is connected to the cooling water circulation line, the cooling water circulation line is connected to a the cooling water storage container (not shown) in the interior of the device body 100, and the cooling water in the cooling water storage container may be circulated. Meanwhile, although not shown, a circulation means such as a pump may be installed on the cooling water circulation line.

Since the high-intensity focused ultrasound operation device 10 having such a structure includes the first cartridge 310 and the second cartridge 320 suitable for different operations which may be selectively mounted to the first operation handpiece 210, an operator may select a cartridge, which may conduct a desired operation, from the first and second cartridges 310 and 320 and conduct an operation by mounting the selected cartridge to the first operation handpiece 210. In this case, various operations may be conducted using one device simply by changing a cartridge, when compared to high-intensity focused ultrasound medical devices that may conduct only one operation, thereby realizing a multi-functional ultrasound medical device structure.

In particular, in the cases of a non-invasive ultrasound operation for face lifting and a non-invasive ultrasound operation for reducing a subcutaneous fat layer, the depth and the intensity of high-intensity focused ultrasound, skin tissue of a subject to be imaged, etc. are completely different and thus it is very difficult to conduct the two operations by means of one device. However, the high-intensity focused ultrasound operation device 10 includes the first image probe 216 which the different first and second cartridges 310 and 320 in the first operation handpiece 210 may share and thus different operations are possible by changing the first and second cartridges 310 and 320, thereby addressing such a technical barrier.

As described above, the high-intensity focused ultrasound operation device 10 according to an embodiment of the present invention including the first cartridge set 300 composed of the first and second cartridges 310 and 320, etc. having different operation purposes may conduct a desired operation, according to operation purpose, by selecting a cartridge, which may conduct a desired operation, from the first and second cartridges 310 and 320 and mounting the same to the first operation handpiece 210. Accordingly, the high-intensity focused ultrasound operation device according to the present invention may conduct two or more high-intensity focused ultrasound operations, using only one device, by providing operation handpieces having various operation purposes and then conduct an operation by means of a handpiece that may conduct a desired operation of a face lifting operation or a skin tightening operations and an operation for reducing or removing a subcutaneous fat layer. In addition, the high-intensity focused ultrasound operation device according to an embodiment of the present invention may include cartridges, compatible with the operation handpiece, having operation conditions suitable for subjects to be operated upon, and a cartridge selected therefrom is mounted to the operation handpiece and used for an operation. Accordingly, patient-specific operations may be conducted by means of only one device through cartridge changing.

Subsequently, the first cartridge set 300 according to an embodiment of the present invention is described in detail. Here, the same contents as those for the high-intensity focused ultrasound operation device 10 previously described may be omitted or simplified.

Figure 4:
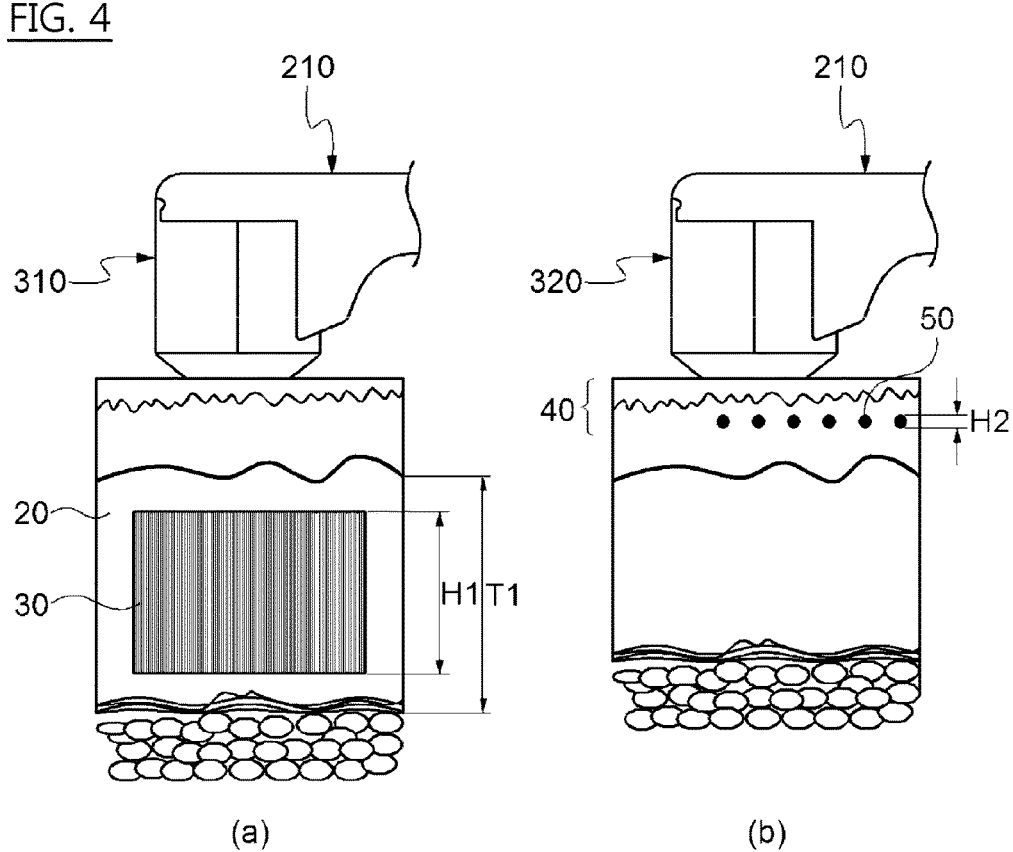
FIG. 4 is a view illustrating first and second cartridges according to an embodiment of the present invention.
Figure 5:
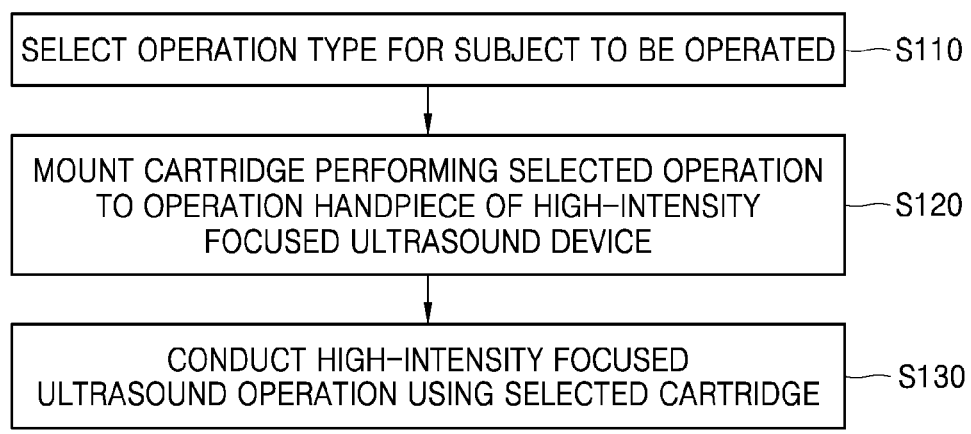
FIG. 5 is a flowchart schematically illustrating a high-intensity focused ultrasound operation method using a first operation handpiece illustrated in FIG. 1.
Figure 6:
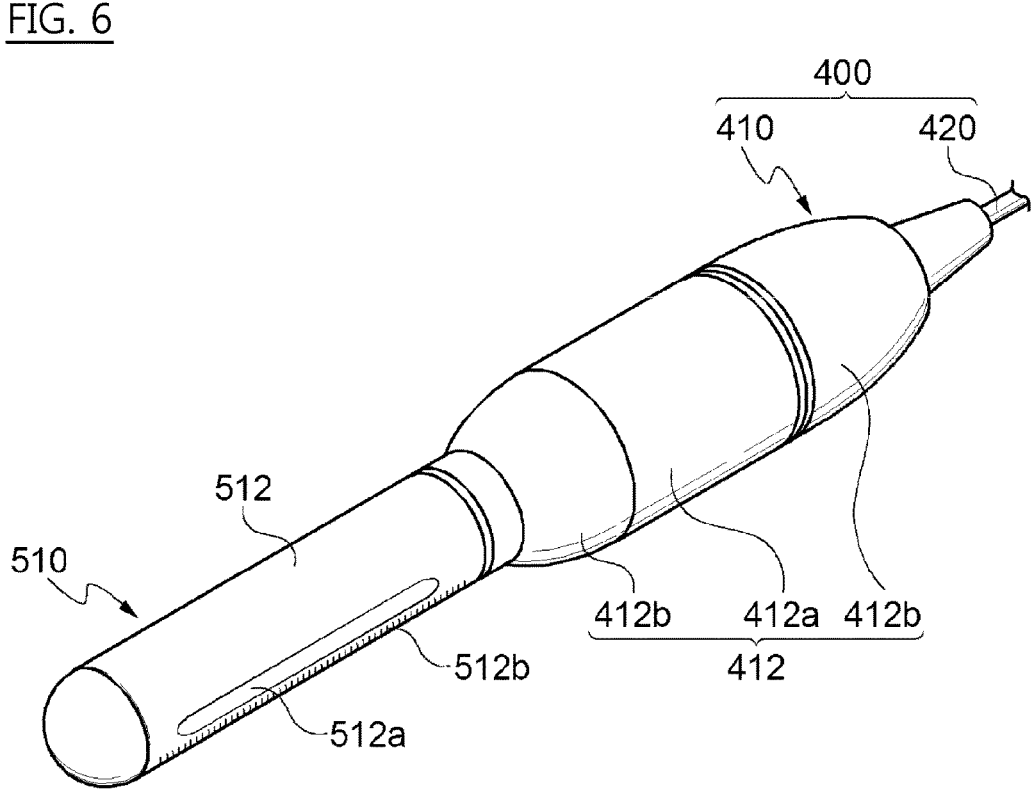
FIG. 6 is a perspective view illustrating a second operation handpiece and a third cartridge illustrated in FIG. 1.
Figure 7:
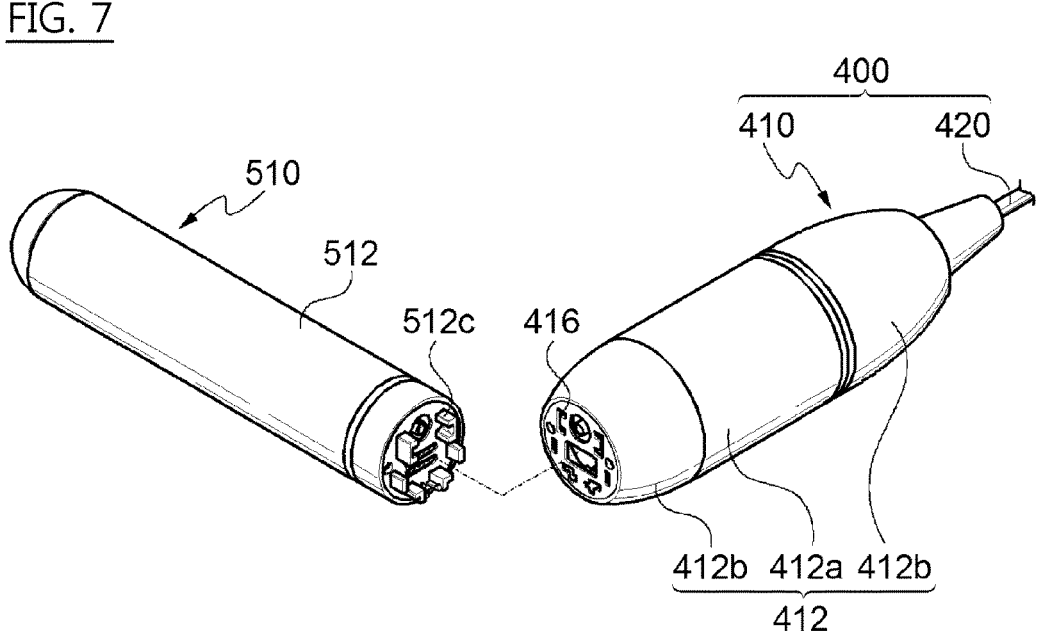
FIG. 7 is a view illustrating a mutual coupling process of a second operation handpiece and a third cartridge illustrated in FIG. 6.

Referring to FIG. 4(a), the first cartridge 310 according to an embodiment of the present invention may be provided for an operation for reducing or removing a subcutaneous fat layer. In an embodiment, the first cartridge 310 may be used when the thickness (T1) of the subcutaneous fat layer 20, as a subject to be operated upon, is 25.0 mm or more. That is, the first cartridge 310 may be set to be operated when the thickness (T1) of the subcutaneous fat layer 20 is 25.0 mm or more. In this case, a patient to be operated upon may be most likely an extremely obese patient. The first cartridge 310 may control a HIFU irradiation depth from a skin surface to about 11.0 mm to 15.0 mm when an up-to-down length H1 of HIFU lesion 30 is controlled to about 8.0 mm to 12.0 mm. When the up-to-down length H1 of the HIFU lesion 30 is less than about 8.0 mm, a reduction efficiency of the subcutaneous fat layer 20 may be decreased. On the other hand, the up-to-down length H1 of the HIFU lesion 30 is greater than about 12.0 mm, a HIFU lesion may be formed outside the subcutaneous fat layer 20. In addition, when the irradiation depth is less than about 11.0 mm or greater than about 15.0 mm, the HIFU lesion 30 may be formed outside the subcutaneous fat layer 20 during operation. Accordingly, the risk that the therapeutic transducer 314 of the first cartridge 310 acts on skin tissue rather than the subcutaneous fat layer 20, although the thickness (T1) of the subcutaneous fat layer 20 is 25.0 mm or more, when the up-to-down length H1 of the HIFU lesion 30 is controlled to about 10.0 mm±2.0 mm and the irradiation depth of the HIFU is controlled to 13.0 mm±2.0 mm may be reduced.

In another embodiment, the first cartridge 310 may be used when the thickness (T1) of subcutaneous fat layer 20, as a subject to be operated, is 7.0 mm or more and less than 25.0 mm or more. That is, the first cartridge 310 may be set to be operated when the thickness (T1) of the subcutaneous fat layer 20 is at least 7.0 mm and less than 25.0 mm. In this case, a patient to be operated upon may most likely be a high extremely obese patient. In this case, the first cartridge 310 may control a HIFU irradiation depth from a skin surface to about 6.0 mm to 10.0 mm when an up-to-down length H1 of HIFU lesion 30 is controlled to about 5.0 mm to 9.0 mm. When the up-to-down length H1 of the HIFU lesion 30 is less than about 5.0 mm, a reduction efficiency of the subcutaneous fat layer 20 may be decreased. On the other hand, the up-to-down length H1 of each of the HIFU lesions 30 is greater than about 9.0 mm, the HIFU lesion 30 may be formed outside the subcutaneous fat layer 20. In addition, when the irradiation depth is less than about 6.0 mm or greater than about 10.0 mm, the HIFU lesion 30 may be separated from the subcutaneous fat layer 20 during operation. Accordingly, the risk that the therapeutic transducer 314 of the first cartridge 310 acts on skin tissue other than the subcutaneous fat layer 20, although the thickness (T1) of the subcutaneous fat layer 20 is 7.0 mm or more and less than 25.0 mm, when the up-to-down length H1 of the HIFU lesion 30 is controlled to about 7.0 mm±2.0 mm and the irradiation depth of the HIFU is controlled to 8.0 mm±2.0 mm may be reduced.

Here, when the therapeutic transducer 314 of the first cartridge 310 moves forward or backward, i.e., performs straight-line back and forth motion, a plurality of the HIFU lesions 30 may be generated. In this case, an interval between the HIFU lesions 30 may be absent or less than 1.0 mm and thus the HIFU lesions 30 resultantly form a straight line or a column without disconnection therein, thereby thermally decomposing the subcutaneous fat layer 20. However, it may be ideal to irradiate HIFU such that the HIFU lesions 30 are maximally adjoined without overlapping since a subject may feel greater pain when the HIFU lesions 30 are overlapped.

Referring to FIG. 4(b), the second cartridge 320 according to an embodiment of the present invention unlike the first cartridge 310 described above may be provided for a face lifting operation or a skin tightening operation. In an embodiment, skin tissue 40 as a subject to be operated by the second cartridge 320 may include dermis, a fascial layer, and an SMAS layer at a depth of about 1.5 mm to 4.5 mm from a skin surface. In this case, the second cartridge 320 may be controlled such that HIFU lesions 50 are generated in a globular, oval or droplet type having a diameter "H2" of about 0.5 mm to 1.5 mm. When the diameters "H2" of the HIFU lesions 50 are less than about 0.5 mm, damage of tissue targeted by HIFU is very slight and thus it may be difficult to obtain face lifting or skin tightening effects through regeneration after intentional skin damage. On the other hand, the diameters of the HIFU lesions 50 are greater than 1.5 mm, the HIFU lesions 50 may be formed in an area outside the skin tissue 40 to be operated upon. In addition, when an irradiated depth is less than about 1.5 mm or greater than about 4.5 mm, the HIFU lesions 50 may be outside the skin tissue 40 to be operated upon. Accordingly, the therapeutic transducer 314 of the second cartridge 320 may preferably control the diameters of the HIFU lesions 50 to about 1.0 mm±0.5 mm and the irradiation depth of HIFU to 1.5 mm to 4.5. Most preferably, the irradiation depth of the HIFU lesions 50 may be one selected from 1.5 mm, 3.0 mm and 4.5 mm and the diameters of the HIFU lesions 50 may be about 1.0 mm±0.2 mm.

Here, when a therapeutic transducer of the second cartridge 320 moves forward or backward, i.e., performs straight-line back and forth motion, a plurality of the HIFU lesions 50 may be generated. In this case, an interval between the HIFU lesions 50 may be about 0.5 mm or more and less than 2.0 mm and thus the HIFU lesions 50 are resultantly spaced apart from each other by a regular interval, thereby being controlled such that a plurality of dots spaced apart from each other along the same line is formed. When an interval between the HIFU lesions 50 is less than 0.5 mm, the HIFU lesions 50 are resultantly connected to each other and thus skin tissue is wounded due to excessive heat, thereby causing problems such as skin necrosis. On the other hand, when an interval between the HIFU lesions 50 is greater than 2.0 mm, the interval between the HIFU lesions 50 becomes too large and thus face lifting or skin tightening effects may be remarkably decreased.

Hereinafter, an operation method of a first operation handpiece of the high-intensity focused ultrasound according to an embodiment of the present invention described above is described in detail. Here, the same descriptions as those for the high-intensity focused ultrasound operation device 10 according to an embodiment of the present invention described above may be omitted or simplified.

Referring to FIGS. 1 to 5, first, an operation type applied to a subject to be operated upon may be selected (S110). For example, an operator (not shown) may select an operation type applied to a subject to be operated upon (not shown). In this case, a selected operation type may be at least one of face lifting or skin tightening operation and an operation for reducing or removing a subcutaneous fat layer. When the operator desires to conduct an operation for reducing or removing a subcutaneous fat layer, the operator may selected the first cartridge 310 according to embodiments described above or other embodiments, considering the thickness of subcutaneous fat layer, the depth of the depth of subcutaneous fat layer and other conditions of a subject to be operated upon. Here, in order to check the thickness of the subcutaneous fat layer, an operator may directly check the thickness of the subcutaneous fat layer by hand or may check a subcutaneous fat layer imaged through an image probe 216 included in the first operation handpiece 210, thus accurately calculating the thickness of the subcutaneous fat layer.

Next, a cartridge to perform the selected operation is selected and a selected cartridge may be mounted to the first operation handpiece 210 of the high-intensity focused ultrasound operation device 10 (S120). For example, when an operator desires to conduct an operation for reducing or removing a subcutaneous fat layer, the first cartridge 310 may be selected from the first cartridge set 300 and mounted to the first operation handpiece 210. Alternatively, when an operator desires to conduct a face lifting or skin tightening operation, the second cartridge 320 may be selected from the first cartridge set 300 and may be mounted to the first operation handpiece 210.

Next, high-intensity focused ultrasound operation may be conducted using a selected cartridge (S130). For example, an operator may conduct a face lifting or skin tightening operation and an operation for reducing or removing a subcutaneous fat layer of a subject by means of the first operation handpiece 210 mounted with one of the first and second cartridges 310 and 320.

As described above, an operation method of the high-intensity focused ultrasound according to an embodiment of the present invention may be conducted, after selecting an operation type for a subject to be operated upon, by selecting the first cartridge 310 or the second cartridge 320 that may perform a desired operation from the first cartridge set 300 and mounting the same to the first operation handpiece 210. Accordingly, the operation method of using the high-intensity focused ultrasound according to the present invention may conduct two or more high-intensity focused ultrasound operations by means of a single device, by mounting a cartridge for a desired operation of a face lifting or skin tightening operation and an operation for reducing or removing a subcutaneous fat layer to a cartridge and using the same after preparing cartridges having various operation purposes in order for compatibility with an operation handpiece. Furthermore, a cartridge for a desired operation of operations for gynecological disease treatment and vaginal contraction described below may be mounted to an operation handpiece and the operation may be conducted. In addition, the operation method of using the high-intensity focused ultrasound according to the present invention may conduct an operation customized for each of patients or operated areas, after preparing cartridges for skin care treatment having various operation conditions, by mounting cartridges suitable for a obesity state or an operated part of a subject to be operated upon to an operation handpiece and conducting an operation for reducing subcutaneous fat layers.

Hereinafter, a second operation handpiece of the high-intensity focused ultrasound according to an embodiment of the present invention and processes of operations for gynecological disease treatment and/or vaginal contraction by means of the same are described in detail. Here, the same description as those of the high-intensity focused ultrasound operation device 10 described above may be omitted or simplified.

Referring to FIG. 1, and FIGS. 6 to 9, operations for gynecological disease treatment and/or vaginal contraction may be conducted using high-intensity focused ultrasound by means of the second handpiece assembly 400 and a second cartridge set 500 of the high-intensity focused ultrasound operation device 10 according to an embodiment of the present invention. Examples of the gynecological disease and vaginal contraction operations may include operations for treating tumors, neoplastic diseases, inflammatory diseases, menstrual disorders, venereal diseases, sexual dysfunction, etc. As an embodiment, the high-intensity focused ultrasound operation device 10 for gynecological disease treatment and vaginal contraction may conduct an operation of densifying or regenerating endopelvic fascia (EPF, 70 of FIG. 11) controlling contraction of a vagina (60 of FIG. 11) in order to treat decreased sexual function or sexual function disorder according to child birth or aging.

Here, the HIFU may form thermal lesions (22 of FIG. 11) by focusing such that ultrasound is concentrated on one focal point. Such thermal lesions 22 may be thermal focuses at a high temperature of about 60° C. or more. Accordingly, the HIFU operation device 10 intentionally impairs or stimulates the endopelvic fascia 70 by forming the thermal lesions 22 on the endopelvic fascia 70 locating at a depth of about 1.0 to 30.0 mm from an inner-wall surface (62 of FIG. 11) of the vagina 60 and promotes recovery or regeneration of the endopelvic fascia 70, thus enhancing contractility of the vagina 6.

The second handpiece assembly 400 may include a second operation handpiece 410 and a second connection cable 420. The second operation handpiece 410 may be manipulated by an operator in order to irradiate HIFU to a subject to be operated upon, and may be provided in a hand-held type in order to provide enhanced convenience to an operator manipulation. For example, the second operation handpiece 410 may include a second handle part 412 such that an operator may hold the second operation handpiece 410. The second handle part 412 may include a second operation switch (not shown) that enables an operator to control HIFU irradiation operation. The second connection cable 420 may electrically and physically connect the second operation handpiece 410 and the device body 100. One end of the second connection cable 420 may be connected to the second operation handpiece 410 and another end thereof may be detachably connected to the device body 100.

The second cartridge set 500 may be a set composed of a plurality of cartridges. For example, the second cartridge set 500 may include third to fifth cartridges 510, 520 and 530, etc. having the same or similar structures. Each of the third to fifth cartridges 510, 520 and 530 may be provided as an insertion part that is inserted into the vagina 60 during operation and, at the same time, as a HIFU irradiating part for irradiating HIFU to skin tissue at a regular depth from an inner-wall surface of the vagina 60.

As an embodiment, operation purposes and conditions of the third to fifth cartridges 510, 520 and 530 may be the same. That is, each of the third to fifth cartridges 510, 520 and 530 may be set such that specific HIFU irradiation intensity, depth and angle, and the sizes and locations of the thermal lesions 22 formed by the HIFU are the same. Accordingly, each of the third to fifth cartridges 510, 520 and 530 may irradiate HIFU to a vaginal inner wall of women during operation under the same or similar conditions and may form the thermal lesions 22. An operator may use a third cartridge 510 among the third to fifth cartridges 510, 520 and 530 by mounting to the second operation handpiece 210 and, when a use period of the third cartridge 510 expires, may use the fourth or fifth cartridge 520 or 530 instead of the third cartridge 510, thus continuously performing the gynecological disease treatment.

As another embodiment, operation purposes and conditions of the third to fifth cartridges 510, 520 and 530 may differ. For example, the third cartridge 510 may be set in order to form relatively large HIFU thermal lesions and the fourth cartridge 520 may be set in order to form relatively small HIFU thermal lesions, compared to the third cartridge 510. Furthermore, the fifth cartridge 530 may be set in order to form relatively small HIFU thermal lesions, compared to the fourth cartridge 520. Alternatively, the third cartridge 510 may be set in order to form the thermal lesions 22 on skin tissue at a relatively shallow depth from the vaginal inner-wall surface 62, and the fourth cartridge 520 may be set in order to form the thermal lesions 22 on skin tissue at a relatively deep depth from the vaginal inner-wall surface 62, compared to the third cartridge 510. Furthermore, the fifth cartridge 530 may be set in order to form the thermal lesions 22 on skin tissue at a relatively deep depth from a vaginal inner-wall surface 62, compared to the fourth cartridge 520.

As described above, since each of the third to fifth cartridges 510, 520 and 530 has the same structure, detailed compositions of the third cartridge 510 are described as an example, and descriptions for the other cartridges 520 and 530 are substituted therewith. The third cartridge 510 may have a cylinder or bar-shape second cartridge body 512 in most cases. The second cartridge body 512 is preferably provided in a type or made of material that may be easily inserted into the vagina 60 of women. Accordingly, a front end of the second cartridge body 512 is convexly protruded and the circumference thereof may be rounded in a smooth curve shape. In addition, the second cartridge body 512 may be made of a material having superior durability, superior corrosion resistance, etc., and harmless to the human body.

A window 512a provided in a longitudinal direction of the second cartridge body 512 may be provided to the circumference of the second cartridge body 512. The window 512a may be composed of a material having high ultrasound transmittance such that HIFU generated from an ultrasound treatment transducer 514 provided to the third cartridge 510 may be efficiently transmitted. In addition, gradations 512b provided in a longitudinal direction of the second cartridge body 512 may be provided to the circumference of the second cartridge body 512. The gradations 512b may be provided so that an operator may grasp a range of the second cartridge body 512 inserted into the vagina. In addition, additional gradations (not shown) provided along a circumference direction of the second cartridge body 512 may be provided to the circumference of the second cartridge body 512. The additional gradations may be provided so that an operator may grasp a rotation degree of the second cartridge body 51, etc. In the present embodiment, the gradations 512b, as an example, is described as a means enabling an operator to estimate an insertion degree of the second cartridge body 512, but a means for estimating an insertion degree of the second cartridge body 512 may be changed or modified.

The third cartridge 510 may be provided detachably from the second operation handpiece 410. For example, second guiders 416 for fastening with the third cartridge 510 may be provided to a front end of the second handle part 412. As an embodiment, the second guiders 416 may be provided as a dented hole or groove in a rear end direction of the second handle part 412. In addition, a portion of the second cartridge body 512, coupled with the second guiders 416 may include fasteners 512c having a shape corresponding to the second guiders 416. The fasteners 512 may be provided as protruded bar-shape structures in order to be inserted into the second guiders 416. In this case, the second guiders 416 and the fasteners 512c may be coupled, separated or rotated in a forcible coupling manner, a screw-bolt coupling manner or a rotatable simple coupling manner. Accordingly, the third cartridge 510 may be mounted to the second operation handpiece 410 by inserting the fasteners 512c into the second guiders 416. In an embodiment, the fasteners 512c may be 360 degree-rotatably coupled in a state inserted into the second guiders 416. In this case, in order to prevent release of a mounted state of the third cartridge 510, the second operation handpiece 410 or each of the third to fifth cartridges 510, 520 and 530 may included an additional locking device (not shown).

Figure 8:
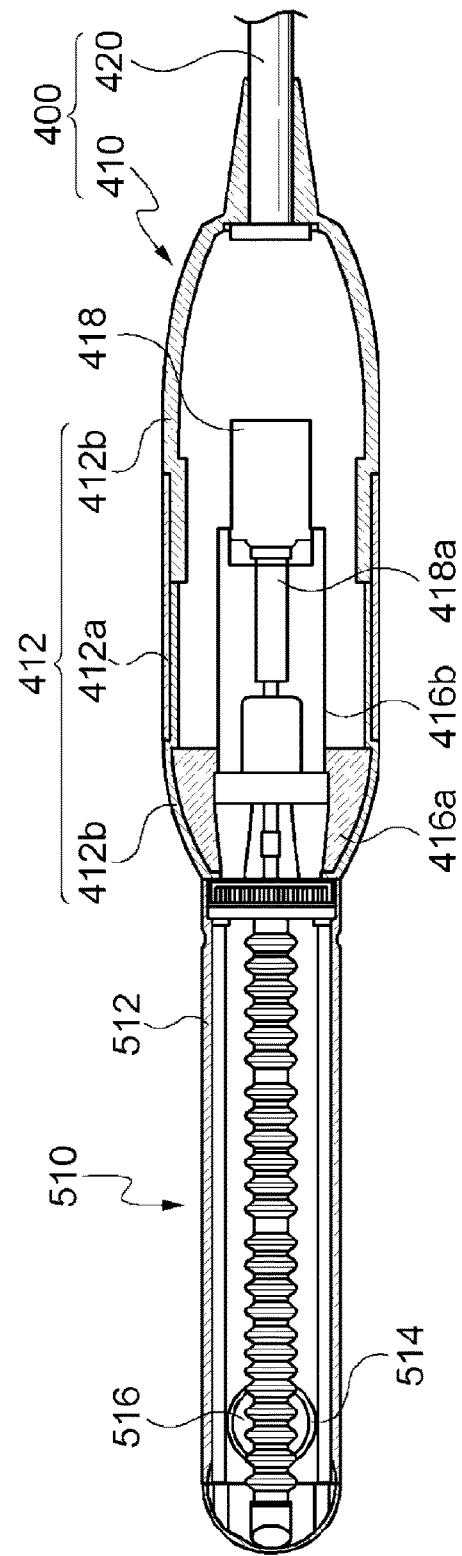
FIG. 8 is a first sectional view illustrating a coupling structure of a second operation handpiece and a third cartridge illustrated in FIG. 6.
Figure 9:
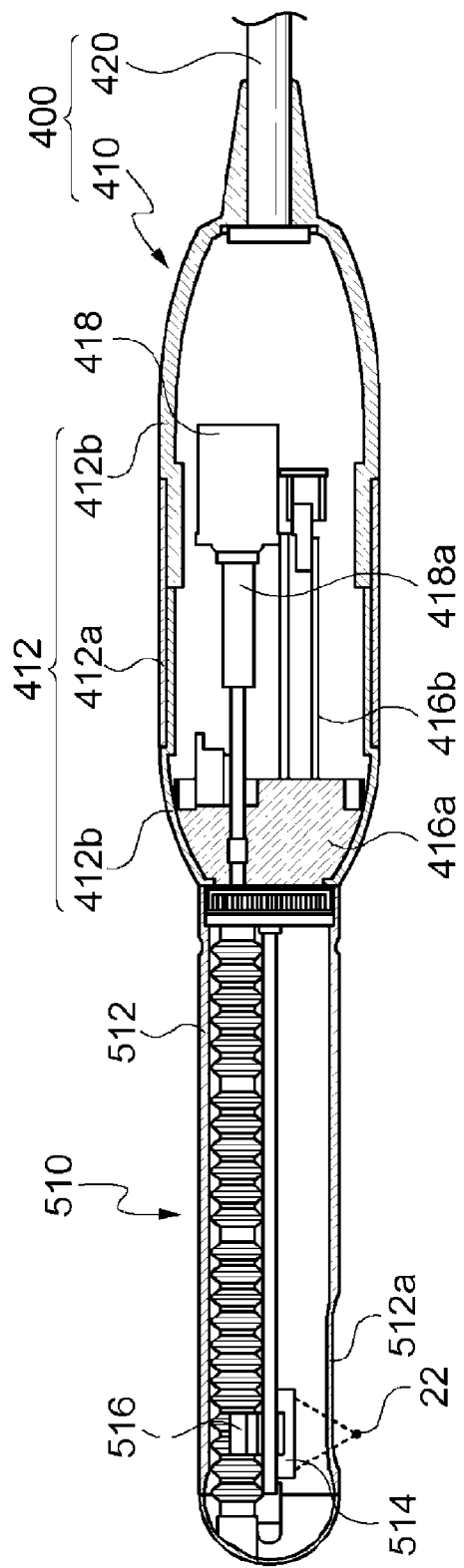
FIG. 9 is a second sectional view illustrating a coupling structure of a second operation handpiece and a third cartridge illustrated in FIG. 6.

The third cartridge 510 may include the ultrasound treatment transducer 514. The ultrasound treatment transducer 514 may include at least one ultrasound transducer generating the HIFU. In an embodiment, as illustrated in FIGS. 8 and 9, the ultrasound treatment transducer 514 may include at least one independent transducer forming a single thermal lesion of HIFU at a regular depth from the inner wall of the vagina 60. In this case, the independent transducer may be provided in order to irradiate the HIFU while moving along the window 512a. In another embodiment, the ultrasound treatment transducer 514 may include at least one transducer array forming multiple thermal lesions of HIFU at a regular depth from the inner wall of the vagina 60. That is, the transducer array may be designed such that a plurality of the thermal lesions 22 is formed in one transducer body. In this case, the transducer array may be designed in order to be fixed to the interior of the second cartridge body 512 without moving, or have a moving distance shorter than the independent transducer.

Meanwhile, each of the third to fifth cartridges 510, 520 and 530 may include a second image probe 516 for imaging skin tissue of an operation subject. The second image probe 516 is provided to image skin tissue on which the thermal lesions 22 are formed, and the composition and the arrangement thereof may be variously changed. As an embodiment, the second image probe 516 may be coupled with the ultrasound treatment transducer 514 to be provided as a single unit with the ultrasound treatment transducer 514. In this case, the image probe 516 may be provided at the center of the ultrasound treatment transducer 514 in order not to disturb an irradiation path of high-intensity focused ultrasound of the ultrasound treatment transducer 514. In another embodiment, the second image probe 516 may be separated from the ultrasound treatment transducer 514 and thus may be separately provided. In this case, the second image probe 516 may be provided at a location that may image skin tissue of an operation subject not while disturbing a moving path of the ultrasound treatment transducer 514.

The second operation handpiece 410 may further include a second driver 418 for front-to-back moving of the ultrasound treatment transducer 514. As an embodiment, a stepper motor, etc. may be used as the second driver 418, and driving thereof may be controlled by the controller 120 described above. In addition, the second driver 418 and the ultrasound treatment transducer 514 may be connected by a predetermined supporter. Accordingly, the second driver 418 is controlled by the controller 120 and thus the ultrasound treatment transducer 514 may move from front to back. As such, the third to fifth cartridges 510, 520 and 530 commonly use the second driver 418 and thus each of the third to fifth cartridges 510, 520 and 530 may move the ultrasound treatment transducer 514 from front to back.

Meanwhile, the second operation handpiece 400 may be provided such that an operator may rotate a cartridge, among the third to fifth cartridges 510, 520 and 530, coupled with the second operation handpiece 400, i.e., the first cartridge 310 in the figure, at a regular angle. As an embodiment, an operator may rotate the third cartridge 510 at 0° to 360° by manually manipulating the second operation handpiece 400. More particularly, the second handle part 412 of the second operation handpiece 400 may be composed of a fixed part 412a and a cartridge-rotating part 412b. An operator may hold the fixed part 412a with one hand (for example, left hand) and may fix the location of the operation handpiece 400 during operation. The cartridge-rotating part 412b is rotatably provided to the fixed part 412a, and may be fastened with one end of the first cartridge 510 in order to rotate with the first cartridge 510 coupled with the second operation handpiece 400. The cartridge-rotating part 412b may be provided such that an operator holds the cartridge-rotating part 412b with another hand (for example, right hand) and rotates the first cartridge 510 during operation. The operation handpiece 200 having such a structure may form the thermal lesions 22 on the total of the vaginal inner wall by enabling an operator to hold the fixed part 412a with a left hand and to rotate the cartridge-rotating part 412b at a regular angle with a right hand, thus enabling the first cartridge 510 to rotate by 0° to 360° with respect to an axis along a longitudinal direction of the first cartridge 510. In an embodiment, a frame fixation part 416a may be fixed to an inner side of the cartridge-rotating part 412b and the second driver 418 may be fixed to the frame 416b coupled with the frame fixation part 416a. Accordingly, the frame 416b and the second driver 418 may rotate together upon rotation of the cartridge-rotating part 412b.

In another embodiment, the third cartridge 510 may automatically rotate by 0° to 360° by simple on-off operation of an operator of the second operation handpiece 400. More particularly, the second driver 418 of the second operation handpiece 410 may rotate the third cartridge 510 by a regular angle with respect to a longitudinal direction of the second cartridge body 512 as a rotation axis. In order to realize this, the second driver 418 may include a rotation motor for rotating the third cartridge 510. Accordingly, the second driver 418 enables the ultrasound treatment transducer 514 to form the thermal lesions 22 at a regular interval along a circumference of the inner wall of the vagina 60, by rotating the third cartridge 510 inside the vagina 60 during operation. Such a cartridge rotation operation enables the total of the inner wall of the vagina 60 to be subjected to HIFU operation in a short time. In this case, the second guiders 416 and the fasteners 512c are preferably provided such that rotation of the cartridge is not disturbed to provide smooth rotation.

In addition, the second driver 418 may move the ultrasound treatment transducer 514 from front to back such that the ultrasound treatment transducer 514 has an operation range of about 10.0 mm to 120.0 mm. More particularly, the second driver 418 may be provided as a stepper motor that is controlled by the controller 120 and moves the ultrasound treatment transducer 514 from front to back by a selected length within a range of about 10.0 mm to 120.0 mm. In this case, the ultrasound treatment transducer 514 may irradiate HIFU during moving within the range. The ultrasound treatment transducer 514 may be set such that HIFU is irradiated at a regular interval in such a way that the thermal lesions 22 form a plurality of dots along the same line or such that HIFU is irradiated in such a way that the thermal lesions 22 form a straight line without an interval.

When a front-to-back moving length of the ultrasound treatment transducer 514 is less than 10.0 mm, an operation area is small during one operation process and thus operation time may be greatly extended. On the other hand, considering the length and type of the vagina 60 or the endopelvic fascia 70 in women, the risk that HIFU is irradiated to skin tissue rather than the endopelvic fascia 70 may be very high when a front-to-back moving distance of the ultrasound treatment transducer 514 is greater than 120.0 mm. Accordingly, when the second driver 418 is set such that the ultrasound treatment transducer 514 moves from front to back within a range of about 10.0 mm to about 120.0 mm, more preferably about 60.0 mm to about 100.0 mm, operation safety may be secured and operation time may be suitably shortened.

Meanwhile, a cooling fluid for cooling heating according to operation of the ultrasound treatment transducer 514 may be provided to each of the third to fifth cartridges 510, 520 and 530. In an embodiment, excessive heating of the ultrasound treatment transducer 514 may be prevented by providing such that the interior of each of the third to fifth cartridges 510, 520 and 530 is filled with cooling water and the cooling water is circulated by a separate cooling water circulation line (not shown). In order to realize this, when the third to fifth cartridges 510, 520 and 530 are mounted to the second operation handpiece 410, the cooling water in the third to fifth cartridges 510, 520 and 530 is connected to the cooling water circulation line, the cooling water circulation line is connected to a cooling water storage container (not shown) in the device body 100, and the cooling water in the cooling water storage container may be circulated. Meanwhile, although not shown, a circulation means such as a pump, etc. (pump) may be installed at the cooling water circulation line.

Operations for gynecological disease treatment and vaginal contraction may be conducted by means of the HIFU operation device 10 according to an embodiment of the present invention described above by, after grasping a vagina state of a subject and selecting a suitable cartridge of the third and fourth cartridges 510 and 520, mounting the selected cartridge to the second operation handpiece 410. In this case, the HIFU operation device 10 may perform operations for gynecological disease treatment and vaginal contraction operation under various operation conditions by changing cartridges, compared to a conventional $CO_2$ laser device performing a single operation condition. Accordingly, the high-intensity focused ultrasound operation device according to an embodiment of the present invention may perform an operation customized for each patient by means of a single device by changing a cartridge since the operation may be conducted by, after preparing a cartridge having an operation condition suitable for a vagina state of a subject to be operated compatibly with an operation handpiece, mounting the selected cartridge on the operation handpiece.

In addition, after mounting one of the third to fifth cartridges 510, 520 and 530 to the HIFU operation device 10 according to an embodiment of the present invention, an operator may move the ultrasound treatment transducer 514 from front to back by means of the second operation handpiece 410 and may form the thermal lesions 22 on an entire inner wall of the vagina 60 while rotating the ultrasound treatment transducer 514 by a regular angle of 0° to 360°. In this case, an operator may irradiate the thermal lesions 22 to an entire inner wall of the vagina 60 by simply manipulating the second operation handpiece 410, thus shortening time taken for operations for gynecological disease treatment and/or vaginal contraction and increasing operation efficiency. Accordingly, the high-intensity focused ultrasound operation device according to an embodiment of the present invention may shorten time taken for operations for gynecological disease treatment and/or vaginal contraction and increase operation efficiency since an operator may form thermal lesions on an entire vaginal inner wall while combining front-to-back movement and rotation of the ultrasound treatment transducer 514 through simple manipulation of the operation handpiece.

In addition, the HIFU operation device 10 according to an embodiment of the present invention described above may directly recover and regenerate the endopelvic fascia 70, which practically takes charge of vaginal contraction, instead of a surface of the vagina 60 using HIFU. In this case, when the HIFU operation device 10 is used, pain is minimal and bleeding does not occur and thus post-operative daily life may be comfortable, compared to conventional $CO_2$ laser operation devices, etc. wherein skin tissue is burned through direct laser irradiation to an inner wall of the vagina 60. Accordingly, since the high-intensity focused ultrasound operation device for gynecological disease treatment and vaginal contraction operations according to the present invention may non-invasively regenerate or recover endopelvic fascia controlling vaginal contraction using high-intensity focused ultrasound, pain is minimal and bleeding hardly occurs, compared to laser devices that directly burn a vaginal inner wall. Therefore, post-operative daily life may be normal.

Hereinafter, the high-intensity focused ultrasound operation method used for the gynecological disease treatment and vaginal contraction operations according to an embodiment of the present invention is described in detail. Here, the same descriptions as those of the HIFU operation device 10 according to an embodiment of the present invention described above may be omitted or simplified.

Figure 10:
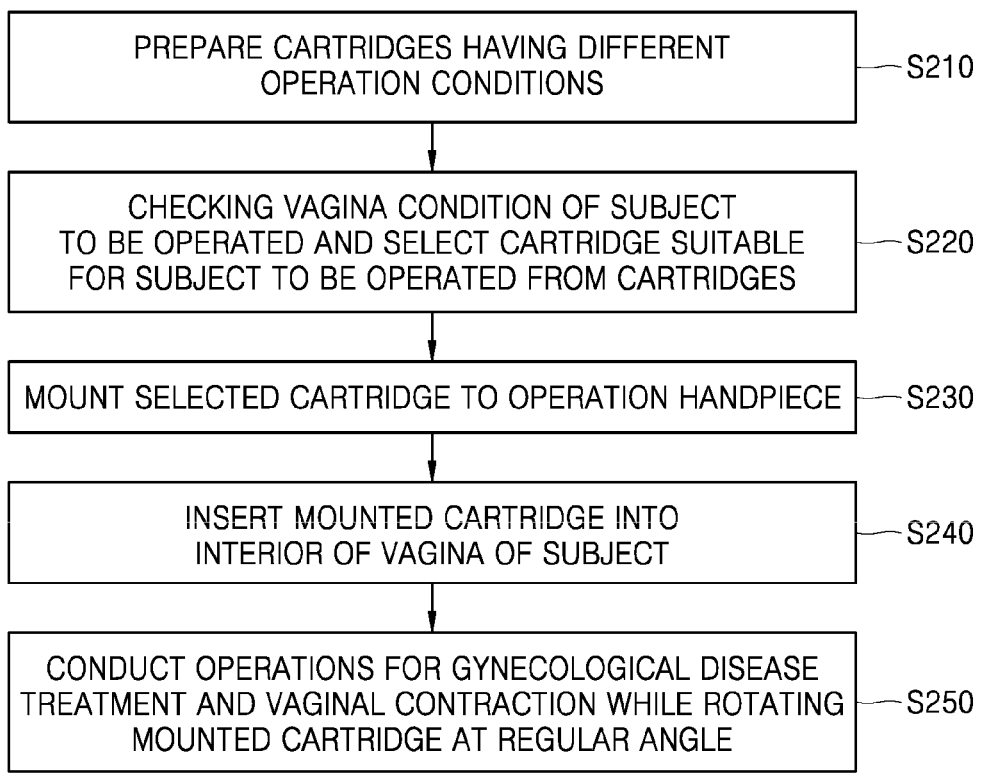
FIG. 10 is a flowchart illustrating an operation process for gynecological disease treatment and vaginal contraction.
Figure 11:
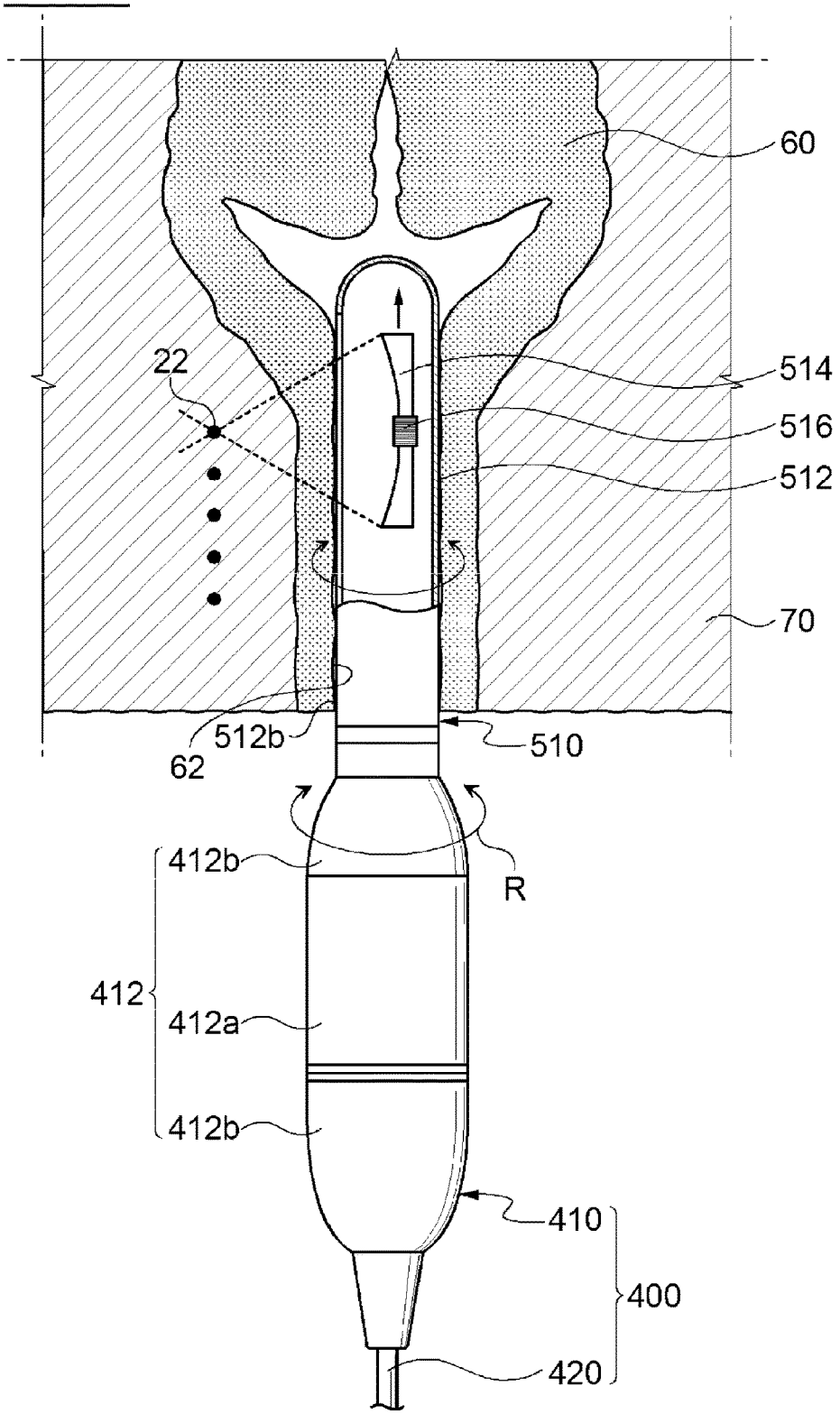
FIG. 11 is a view illustrating an operation process for gynecological disease treatment and vaginal contraction according to an embodiment of the present invention.

Referring to FIGS. 10 and 11, cartridges having different operation conditions may be prepared at S210. For example, the step of preparing the cartridges may include a step of preparing the third to fifth cartridges 510, 520 and 530 having different high-intensity focused ultrasound irradiation conditions. As an embodiment, high-intensity focused ultrasound from the third to fifth cartridges 510, 520 and 530 may have different thermal lesion sizes. In another embodiment, the third to fifth cartridges 510, 520 and 530 may have different high-intensity focused ultrasound irradiation depths, i.e., different thermal lesion generation depths.

After checking a condition of a vagina of a subject to be operated upon, a cartridge suitable for a subject to be operated upon among the cartridges may be selected at S220. For example, an operator (not shown) grasps a state and the shape of a vagina of a subject to be operated upon (not shown) and may select a cartridge having a suitable operation condition from the third to fifth cartridges 510, 520 and 530. Here, a state of a vagina of a subject to be operated upon may be grasped by checking a skin tissue state imaged by the second image probe 516 through the display 110 after coupling one cartridge with the second operation handpiece 410.

A selected cartridge may be mounted to the second operation handpiece 410 at S230. Here, the case that an operator selects the third cartridge 510 is described as an example. For example, an operator may select the third cartridge 510 and may mount the same to the second operation handpiece 410. In this case, an operator inserts the fasteners 512c of the third cartridge 510 into the second guiders 416 of the second operation handpiece 410, thus fastening the third cartridge 510 to the second operation handpiece 410.

The selected cartridge 510 may be inserted into the vagina 60 of an operation subject at S240. In this case, when the first cartridge 510 is located at the interior of the vagina 60, skin tissue of an operation subject is imaged through the second image probe 516 and may be displayed on the display 110. An operator may determine a suitable location of the second operation handpiece 410 by synthesizing the image from the second image probe 516, the gradations 512b provided to the cartridge body 512 of the second cartridge 510, etc.

In addition, the operations for gynecological disease treatment and vaginal contraction may be conducted while rotating the cartridge 510 mounted at a regular angle at S250. More particularly, when a location of the second operation handpiece 410 is determined, an operator may manipulate the controller 120, the second operation switch (not shown), etc. such that the thermal lesions 22 of the high-intensity focused ultrasound are formed at a predetermined location of the endopelvic fascia 70 by the ultrasound treatment transducer 514. In this case, the third cartridge 510 performs straight-line back-and-forth motion and rotation by manual manipulation, etc. of the second driver 418 or an operator and thus a plurality of the thermal lesions 22 may be three-dimensionally formed on the endopelvic fascia 70.

More particularly, an operator holds and fastens the fixed part 412a of the second operation handpiece 410 with one hand, and then the other hand may turn on/off an operation switch (not shown) provided at the second operation handpiece 410. Accordingly, while the ultrasound treatment transducer 514 in the cartridge 510 moves forward along a longitudinal direction of the third cartridge 510, the thermal lesions 22 may be formed on skin tissues of the vaginal inner wall along a virtual first line. When formation of the thermal lesions 22 is completed due to the front-to-back movement, an operator may rotate the cartridge-rotating part 412b of the second operation handpiece 410 at a regular angle with the other hand. The third cartridge 510 may rotate at a regular angle along a rotation direction (R) with respect to a rivet of the third cartridge 510 due to rotation of the cartridge-rotating part 412b. In addition, the operator enables the ultrasound treatment transducer 514 to be parallel to the first line and the thermal lesions 22 may be formed along a second line spaced apart from the first line at a regular interval, by operating the operation switch or the foot switch.

By repeating the operation sequence, the thermal lesions 22 may be formed as a plurality of dots spaced apart from one another at a regular depth along the same line over all areas of the endopelvic fascia 70. Accordingly, the endopelvic fascia 70 is properly damaged and stimulated by the thermal lesions 22 and the damaged skin tissue is recovered and regenerated, thereby densifying skin tissue of the endopelvic fascia 70.

As described above, the high-intensity focused ultrasound according to an embodiment of the present invention operation may be operated by grasping a state of a subject to be operated upon, selecting a cartridge, e.g., the cartridge 510, having a desired operation condition from the second cartridge set 500 and mounting the same to the second operation handpiece 410. Accordingly, operation may be conducted by preparing a cartridge having an operation condition suitable for a vagina state of a subject compatibly with an operation handpiece and mounting a selected cartridge to the operation handpiece. Therefore, an operation customized for a patient may be conducted by changing a cartridge by means of a single device.

In addition, through the high-intensity focused ultrasound operation method according to an embodiment of the present invention, an operator may evenly form the thermal lesions 22 over an entire inner wall of the vagina 60 by moving, from back-to-forth, or rotating, at a regular angle within a range of 0° to 360°, the ultrasound treatment transducer 514 in the cartridge mounted to the second operation handpiece 41, through simple manipulation. Accordingly, an operator may form thermal lesions over an entire vaginal inner wall while combining front-to-back movement and rotation of the ultrasound treatment transducer, by simply manipulating the operation handpiece, thereby shortening time taken for gynecological disease treatment and/or vaginal contraction operations and enhancing operation efficiency.

In addition, the high-intensity focused ultrasound operation method according to an embodiment of the present invention may directly recover and regenerate the endopelvic fascia 70 primarily controlling vaginal contraction, instead of a surface of the vagina 60, using HIFU. Accordingly, when the method is used, pain is minimal and bleeding does not occur, compared to a laser device that directly burns a vaginal inner wall. Therefore, the patient can live an ordinary life after operation.

DESCRIPTION OF SYMBOLS

10: high-intensity focused ultrasound operation device. 12, 22: thermal lesion. 20: subcutaneous fat layer. 30, 50: HIFU lesion. 40: skin tissue as operation subject. 60: vagina. 70: endopelvic fascia. 100: device body. 110: display. 120: controller. 200: first handpiece assembly. 210: first operation handpiece. 212: first handle part. 214: first guider. 216: first image probe. 218: first driver. 220: first connection cable. 300: first cartridge set. 310: first cartridge. 312: first cartridge body. 314: therapeutic transducer. 316: supporter. 400: second handpiece assembly. 410: second operation handpiece. 412: second handle part. 416: second guider. 418a: second driver. 418: second connection cable. 500: second cartridge set. 510: third cartridge. 512: second cartridge body. 514: ultrasound treatment transducer. 516: second image probe. 520: fourth cartridge.

INDUSTRIAL APPLICABILITY

A high-intensity focused ultrasound operation device and an operation method thereof according to an embodiment of the present invention may be utilized in various operations such as obesity treatment, skin beauty treatment, gynecological disease treatment, etc.

The invention claimed is:

1. A high-intensity focused ultrasound operation device, comprising:
    a handle part for manipulation by an operator, wherein the handle part comprises a fixed part and a cartridge-rotating part configured to be rotatably coupled with the fixed part;
    a plurality of cartridges configured to be selectively coupled with the cartridge-rotating part of the handle part;
    an ultrasound treatment transducer provided inside each of the plurality of cartridges and configured to generate high-intensity focused ultrasound (HIFU) configured to form a thermal lesion, where a cartridge selected from the plurality of cartridges is mounted at a front end of the cartridge-rotating part of the handle part, and the cartridge-rotating part is configured to rotate the selected cartridge among the plurality of cartridges, and
    a driver configured to drive the ultrasound treatment transducer of the selected cartridge of the plurality of cartridges; and
    a controller configured to control the driver,
    wherein the selected cartridge of the plurality of cartridges is provided as an insertion part configured to be inserted in a human body during operation and as a HIFU irradiating part for irradiating the HIFU,
    wherein the driver is arranged inside of the cartridge-rotating part and comprises a stepper motor enabling the ultrasound treatment transducer of the selected cartridge of the plurality of cartridges to perform straight-line back-and-forth motion within a range of 10.0 mm to 120.0 mm.

2. The high-intensity focused ultrasound operation device according to claim 1, wherein the ultrasound treatment transducer of the selected cartridge comprises at least one independent transducer that forms at least one thermal lesion with the HIFU at a location spaced apart from a vaginal inner-wall surface by a predetermined distance.

3. The high-intensity focused ultrasound operation device according to claim 1, wherein the ultrasound treatment transducer of the selected cartridge comprises at least one transducer array that forms one or multiple thermal lesions with the HIFU at a location spaced apart from a vaginal inner-wall surface by a predetermined distance.

4. The high-intensity focused ultrasound operation device according to claim 1, wherein at least one of the plurality of cartridges has a cylinder or bar shape and comprises a window, which is formed in a longitudinal direction of the at least one of the plurality of cartridges at a circumference of the at least one of the plurality of cartridges, and the HIFU generated from the ultrasound treatment transducer is transmitted through the window.

5. The high-intensity focused ultrasound operation device according to claim 1, wherein the ultrasound treatment transducer of the selected cartridge irradiates the HIFU to a depth of 1.0 to 30.0 mm from a vagina surface.

6. The high-intensity focused ultrasound operation device according to claim 1, wherein at least one of the plurality of cartridges has a cylinder or bar shape having a circumference surface on which gradations are provided in a longitudinal direction of the cylinder or bar shaped cartridge, and the driver is arranged inside of the cartridge-rotating part and comprises a rotation motor configured to rotate the ultrasound treatment transducer of the selected cartridge of the plurality of cartridges, via a supporter, within a range of 30 to 360 degree to form the thermal lesion on skin tissues at a predetermined distance from a surface of a vaginal inner wall.

7. The high-intensity focused ultrasound operation device according to claim 1, wherein the controller controls the driver such that thermal lesions caused by the HIFU of the ultrasound treatment transducer of the selected cartridge form a straight line during operation.

8. The high-intensity focused ultrasound operation device according to claim 1, wherein the controller controls the driver such that thermal lesions caused by the HIFU of the ultrasound treatment transducer of the selected cartridge form a plurality of dots arranged as a straight line during operation.

9. The high-intensity focused ultrasound operation device according to claim 1, further comprising: an image probe provided at the plurality of cartridges and configured to image an area irradiated with the HIFU of the corresponding ultrasound treatment transducer of the plurality of cartridges.

10. The high-intensity focused ultrasound operation device according to claim 9, wherein the image probe is coupled to the corresponding ultrasound treatment transducer.

11. The high-intensity focused ultrasound operation device according to claim 1, further comprising:

a cooling fluid circulation line for supplying cooling fluid to the plurality of cartridges and retrieving the supplied cooling fluid.

12. A high-intensity focused ultrasound operation device, comprising:
 a handle part for manipulation by an operator, wherein the handle part comprises a fixed part and a cartridge-rotating part configured to be rotatably coupled with the fixed part;
 a plurality of cartridges configured to be selectively coupled with the cartridge-rotating part of the handle part;
 an ultrasound treatment transducer provided inside each of the plurality of cartridges and configured to generate high-intensity focused ultrasound (HIFU) configured to form a thermal lesion, where a cartridge selected from the plurality of cartridges is mounted at a front end of the cartridge-rotating part of the handle part, and the cartridge-rotating part is configured to rotate the selected cartridge among the plurality of cartridges;
 a driver configured to drive the ultrasound treatment transducer of the selected cartridge among the plurality of cartridges; and
 a controller configured to control the driver,
 wherein the selected cartridge of the plurality of cartridges has a cylinder or bar shape, and the driver is arranged inside of the cartridge-rotating part and comprises a rotation motor configured to rotate the ultrasound treatment transducer of the selected cartridge of the plurality of cartridges, via a supporter, within a range of 30 to 360 degrees so that the selected cartridge, after actuation to form thermal lesions on skin tissues of a vaginal inner wall along a virtual first line, is configured to be rotated and then actuated to form the thermal lesions along at least a second line spaced apart from the first line at a regular interval.

13. The high-intensity focused ultrasound operation device according to claim 12,
 wherein the ultrasound treatment transducer of the selected cartridge comprises at least one transducer array configured to form multiple thermal lesions with the HIFU at a location spaced apart from a vaginal inner-wall surface by a predetermined distance when the ultrasound treatment transducer of the selected cartridge moves in front and rear directions in a longitudinal direction of the selected cartridge.

14. The high-intensity focused ultrasound operation device according to claim 12, wherein the ultrasound treatment transducer of the selected cartridge of the plurality of cartridges comprises at least one transducer array configured to form multiple thermal lesions with the HIFU, and
 wherein the rotation motor is configured to rotate the ultrasound treatment transducer of the selected cartridge among the plurality of cartridges, and the ultrasound treatment transducer of the selected cartridge is configured to form the multiple thermal lesions on skin tissues at a predetermined depth from a vaginal inner wall surface along a virtual first line, and configured to form the multiple thermal lesions on the skin tissues of the vaginal inner wall surface along a second line spaced apart from the first line at a regular interval.

15. The high-intensity focused ultrasound operation device according to claim 14, wherein each of the thermal lesions forms a straight line or the multiple thermal lesions form a column.

16. A high-intensity focused ultrasound operation device, comprising:
 a handle part for manipulation by an operator, wherein the handle part comprises a fixed part and a cartridge-rotating part configured to be rotatably coupled with the fixed part;
 a plurality of cartridges configured to be selectively coupled with the cartridge-rotating part of the handle part;
 an ultrasound treatment transducer provided inside each of the plurality of cartridges and configured to generate high-intensity focused ultrasound (HIFU) configured to form a thermal lesion, where a cartridge selected from the plurality of cartridges is mounted at a front end of the cartridge-rotating part of the handle part, and the cartridge-rotating part is configured to rotate the selected cartridge among the plurality of cartridges;
 a driver configured to drive the ultrasound treatment transducer of the selected cartridge among the plurality of cartridges; and
 a controller configured to control the driver,
 wherein the selected cartridge of the plurality of cartridges is provided as an insertion part configured to be inserted in a human body during operation and as a HIFU irradiating part for irradiating the HIFU, and
 wherein a guider is provided at the front end of the cartridge-rotating part and configured to fasten to the selected cartridge of the plurality of cartridges such that the cartridge-rotating part and the selected cartridge rotate together.

\* \* \* \* \*